US00PP15846P2

(12) United States Plant Patent
Sakazaki

(10) Patent No.: US PP15,846 P2
(45) Date of Patent: Jul. 12, 2005

(54) ***PHLOX* PLANT NAMED 'USPHL03'**

(50) Latin Name: *Phlox hybrida*
Varietal Denomination: USPHL03

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 96 days.

(21) Appl. No.: 10/827,547

(22) Filed: Apr. 19, 2004

(51) Int. Cl.[7] ..... A01H 5/00
(52) U.S. Cl. ..... Plt./320
(58) Field of Search ..... Plt./320

*Primary Examiner*—Anne Marie Grunberg
(74) *Attorney, Agent, or Firm*—C. A. Whealy

(57) ABSTRACT

A new and distinct cultivar of *Phlox* plant named 'USPHL03', characterized by its upright and outwardly spreading plant habit; vigorous growth habit; attractive dark purple-colored flowers with a red purple-colored star pattern at the center; freely and continuous flowering habit; and good garden performance.

1 Drawing Sheet

Botanical classification/cultivar designation: *Phlox hybrida* cultivar USPHL03.

BACKGROUND OF THE INVENTION

The present Invention relates to a new and distinct cultivar of *Phlox* plant, botanically known as *Phlox hybrida*, and hereinafter referred to by the cultivar name USPHL03.

The new *Phlox* is a product of a planned breeding program conducted by the Inventor in Hikone Shiga, Japan. The objective of the breeding program was to create new pot-type *Phlox* cultivars with numerous flowers with attractive coloration.

The new *Phlox* originated from a cross-pollination made by the Inventor on Apr. 25, 2000 in Hikone Shiga, Japan of two unidentified selections of *Phlox hybrida*, not patented. The new *Phlox* was discovered and selected by the Inventor as a flowering plant within the progeny of the stated cross-pollination in a controlled environment in Bonsall, Calif., on Jun. 24, 2001.

Asexual reproduction of the new cultivar by terminal cuttings at Bonsall, Calif. since Jul. 5, 2001, has shown that the unique features of this new *Phlox* are stable and reproduced true to type in successive generations.

SUMMARY OF THE INVENTION

Plants of the cultivar USPHL03 have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'USPHL03'. These characteristics in combination distinguish 'USPHL03' as a new and distinct cultivar:

1. Upright and outwardly spreading plant habit.
2. Vigorous growth habit.
3. Attractive dark purple-colored flowers with a red purple-colored star pattern at the center.
4. Freely and continuous flowering habit.
5. Good garden performance.

Plants of the new *Phlox* differ from plants of the parent selections in the following characteristics:

1. Plants of the new *Phlox* are more vigorous than plants of the parent selections.
2. Plants of the new *Phlox* have larger flowers than plants of the parent selections.
3. Plants of the new *Phlox* flower for a longer period of time than plants of the parent selections.

Plants of the new *Phlox* can be compared to the other selections of *Phlox hybrida*, not patented, know to the Inventor. In side-by-side comparisons conducted in Hikone Shiga, Japan, plants of the new *Phlox* differed from plants of other selections of *Phlox hybrida* known to the Inventor in the following characteristics:

1. Plants of the new *Phlox* were more vigorous than plants of other selections of *Phlox hybrida* known to the Inventor.
2. Plants of the new *Phlox* flowered for a longer period of time than plants of other selections of *Phlox hybrida* known to the Inventor.
3. Plants of the new *Phlox* were more high-temperature tolerant than plants of other selections of *Phlox hybrida* known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Phlox*.

The photograph at the top of the sheet comprises a side perspective view of a typical flowering plant of 'USPHL03' grown in a container.

The photograph at the bottom of the sheet is a close-up view of typical flowers of 'USPHL03'.

DETAILED BOTANICAL DESCRIPTION

The aforementioned photographs, following observations and measurements describe plants grown in Bonsall, Calif., in an outdoor nursery and under commercial production practices during the summer. Plants were about four weeks when the photographs and description were taken. During the production of the plants, day temperatures ranged from 18 to 35° C. and day temperatures ranged from 7 to 18° C. In the following description, color references are made to The Royal Horticultural Society Colour Chart, 1995 Edition, except where general terms of ordinary dictionary significance are used.

Botanical classification: *Phlox hybrida* cultivar USPHL03.

Parentage:

*Female parent.*—Unidentified selection of *Phlox hybrida*, not patented.

*Male parent.*—Unidentified selection of *Phlox hybrida*, not patented.

Propagation:

*Type cutting.*—Vegetative cuttings.

*Time to initiate roots.*—About one to two weeks.

*Time to produce a rooted young plant.*—About three to four weeks.

*Root description.*—Fine, fibrous.

*Rooting habit.*—Freely branching; moderately dense.

Plant description:

*Plant form/habit.*—Upright and outwardly spreading plant habit; broad inverted triangle; vigorous growth habit. Freely branching with about five main stems per plant each with multiple secondary lateral branches.

*Plant height.*—About 16 cm.

*Plant width* (*spread*).—About 38 cm.

*Lateral branches.*—Length: About 20 cm. Diameter: About 3 mm. Internode length: About 1.2 cm. Strength: Strong. Texture: Pubescent. Color: 146B.

*Foliage description.*—Arrangement: Alternate, simple; sessile. Length: About 2.5 cm. Width: About 8 mm. Shape: Lanceolate. Apex: Acuminate. Base: Slightly auriculate; clasping. Margin: Entire. Texture, upper and lower surfaces: Slightly coarse; pubescent. Venation pattern: Pinnate; arcuate. Color: Developing leaves, upper and lower surfaces: 146A. Fully expanded leaves, upper and lower surfaces: 147A. Venation, upper surface: 147A. Venation, lower surface: 147B.

Flower description:

*Flower type/habit.*—Single, rounded salverform flowers arranged in terminal panicles; flowers face upright and outward. Panicles roughly hemispherical in shape. Freely flowering habit with about 24 to 36 flower buds and flowers per lateral branch.

*Fragrance.*—None detected.

*Natural flowering season.*—Continuously flowering from spring through fall in Southern California Flowers persistent.

*Posproduction longevity.*—Flowers last about four to five days on the plant.

*Inflorescence height.*—About 3.5 cm.

*Inflorescence diameter.*—About 5 cm.

*Flower buds.*—Height: About 1.5 cm. Diameter: About 3 mm. Shape: Elongated ovoid. Color: 198D overlain with 185D.

*Flowers.*—Diameter: About 2.5 cm. Depth: About 1.6 cm.

*Petals.*—Quantity per flower: Typically five in a single whorl; petals fused at the base into a narrow tube. Length: About 1.2 cm. Width: About 1.1 cm. Shape: Obovate. Apex: Broadly acute. Margin: Entire. Aspect: Mostly flat; slightly undulate. Texture, upper and lower surfaces: Smooth, glabrous; satiny. Color: Developing petals, upper surface: 78A; towards the base, 82A; central star pattern, 66A. Developing petals, lower surface: 155D. Fully expanded petals, upper surface: 77A; central star pattern, 74A. Fully expanded petals, lower surface: 155D overlain with 77B.

*Sepals.*—Quantity per flower: Typically five in a single whorl, fused; narrow tubular calyx. Length: About 5 mm. Width: About 1 mm. Shape: Apicular; recurved. Apex: Acuminate. Texture, upper and lower surfaces: Smooth, glabrous. Color, upper and lower surfaces: 137A.

*Peduncles.*—Length: About 2 cm. Diameter: About 2 mm. Orientation: Erect to about 45° from vertical. Strength: Strong. Color: 146B.

*Pedicels.*—Length: About 1 cm. Diameter: About 1 mm. Orientation: About 45° from vertical. Strength: Strong. Color: 146A.

*Reproductive organs.*—Stamens: Quantity per flower: Typically five. Anther shape: Oblong. Anther size: About 1 mm by 2 mm. Anther color: 15A. Pollen amount: Scarce. Pollen color: 15A. Pistils: Quantity per flower: Typically one. Pistil length: About 4 mm. Stigma shape: Bi-parted. Stigma color: 10B. Style length: About 1.5 cm. Style color: 155D. Ovary color: 145A.

Disease/pest resistance: Plants of the new *Phlox* have been noted to be resistant to Powdery Mildew. Plants of the new *Phlox* have not been noted to be resistant to other pathogens and pests common to *Phlox*.

Garden performance: Plants of the new *Phlox* have been observed to have good garden performance and tolerate rain, wind and temperatures ranging from −3 to 38° C.

It is claimed:

1. A new and distinct cultivar of *Phlox* plant named 'USPHL03', as illustrated and described.

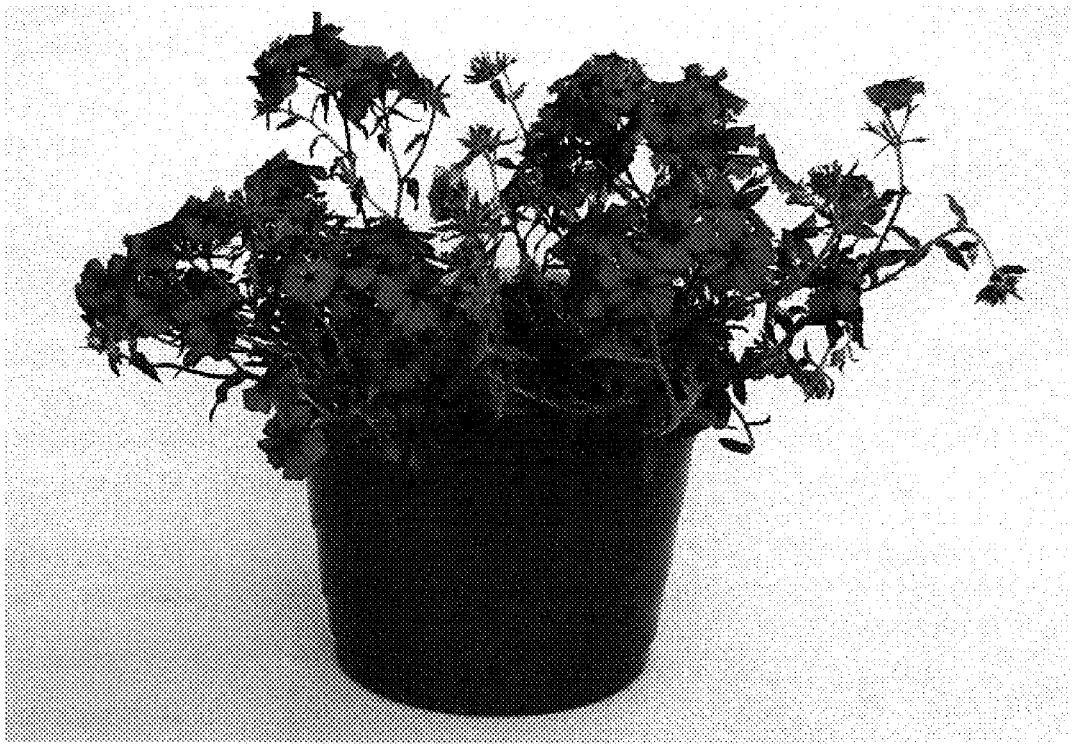
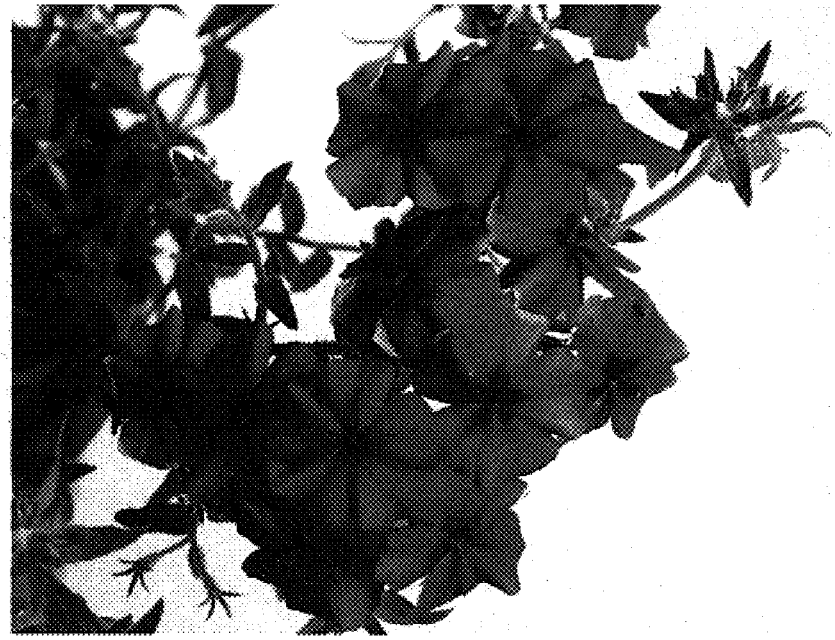

* * * * *